United States Patent
Muller et al.

(10) Patent No.: US 10,398,397 B2
(45) Date of Patent: Sep. 3, 2019

(54) CONTRAST-ENHANCED X-RAY IMAGE GUIDED BIOPSY SYSTEM AND METHOD

(71) Applicants: GENERAL ELECTRIC COMPANY, Schenectady, NY (US); Gustave Roussy, Villejuif (FR)

(72) Inventors: Serge Louis Wilfrid Muller, Buc (FR); Razvan Gabriel Iordache, Buc (FR); Sylvie Saab-Puong, Buc (FR); Ann-Katherine Carton, Buc (FR); Clarisse Dromain, Gometz-le-Châtel (FR)

(73) Assignee: General Electric Company, Schenectady, NY (US)

( * ) Notice: Subject to any disclaimer, the term of this patent is extended or adjusted under 35 U.S.C. 154(b) by 1139 days.

(21) Appl. No.: 14/587,522

(22) Filed: Dec. 31, 2014

(65) Prior Publication Data
US 2016/0183896 A1 Jun. 30, 2016

(51) Int. Cl.
*A61B 6/00* (2006.01)
*A61B 6/02* (2006.01)
(Continued)

(52) U.S. Cl.
CPC ............... *A61B 6/481* (2013.01); *A61B 6/12* (2013.01); *A61B 6/461* (2013.01); *A61B 6/482* (2013.01);
(Continued)

(58) Field of Classification Search
CPC .. A61B 6/02; A61B 6/025; A61B 6/03; A61B 6/032; A61B 6/4435; A61B 6/461;
(Continued)

(56) References Cited

U.S. PATENT DOCUMENTS 6,714,621 B2   3/2004   Rick et al.
6,848,826 B2   2/2005   Marie et al.
(Continued)

FOREIGN PATENT DOCUMENTS

DE   102011087127 A1   5/2013
FR       2971412 A1 *  8/2012   ............. A61B 6/025
(Continued)

OTHER PUBLICATIONS

International Search Report and Written Opinion for PCT/US2015/062618, dated Apr. 11, 2016, 12 pages.

*Primary Examiner* — Carolyn A Pehlke
(74) *Attorney, Agent, or Firm* — Boyle Fredrickson, S.C.

(57) ABSTRACT

In the present invention, an imaging system and method for providing contrast-enhanced X-ray images of tissue includes an energy source in communication with a detector operable to generate radiological images of the tissue injected with the contrast agent, a display and a computer connected to the display and to receive the acquired images from the detector. The system is operable to acquire a number of first images of the contrast agent in the tissue, wherein the number of first images are single energy images, and a number of second images corresponding to the number of first images, wherein the second images are each a single energy image with an energy level opposite that for the first images. The first and second images are combined to generate a contrast-enhanced image with reduced exposure of the tissue and reduced time for completion of the procedure.

16 Claims, 7 Drawing Sheets

(51) Int. Cl.
  *A61B 6/12* (2006.01)
  *A61B 10/04* (2006.01)
(52) U.S. Cl.
  CPC .............. *A61B 6/488* (2013.01); *A61B 6/502* (2013.01); *A61B 6/025* (2013.01); *A61B 2010/045* (2013.01)
(58) Field of Classification Search
  CPC ......... A61B 6/481; A61B 6/482; A61B 6/488; A61B 6/502; A61B 6/5235
  See application file for complete search history.

(56) References Cited

U.S. PATENT DOCUMENTS

| | | |
|---|---|---|
| 7,693,254 B2 | 4/2010 | Muller et al. |
| 2006/0269040 A1 | 11/2006 | Mertelmeier |
| 2007/0189448 A1 | 8/2007 | Muller et al. |
| 2008/0167552 A1 | 7/2008 | Bouchevreau et al. |
| 2013/0044861 A1 | 2/2013 | Muller et al. |
| 2014/0072096 A1 | 3/2014 | Hoernig |

FOREIGN PATENT DOCUMENTS

| | | |
|---|---|---|
| WO | 2006119426 A2 | 11/2006 |
| WO | 2012122399 | 9/2012 |

\* cited by examiner

CONTRAST-ENHANCED X-RAY IMAGE GUIDED BIOPSY SYSTEM AND METHOD

BACKGROUND OF INVENTION

Embodiments of the invention relate generally to X-ray medical imaging, and more particularly to systems and methods to perform a spectral mammography (SM) such as 2D/3D dual-energy contrast-enhanced (CE), or digital breast tomosynthesis (DBT) guided biopsy exams.

Spectral mammography (SM) is an X-ray imaging modality used to scan breasts for screening, diagnosis and/or interventional examinations. The effectiveness of spectral mammography is affected by numerous factors, one of which is the two-dimensional (2D) rendering of images obtained using SM.

Alternative systems to SM are also known for breast imaging. For example, a digital breast tomosynthesis (DBT) or mammography-tomography (mammo-tomo) system is a dedicated mammography system that acquires several (e.g., tens of) angularly offset projection images and reconstructs three-dimensional (3D) image datasets.

To further assist in the detection and treatment of abnormalities in the breast, and in particular to enhance the ability of the SM and DBT systems to differentiate cancers in the breast from other abnormalities, contrast agents, such as iodine, can be injected into the patient that travel to the region of interest (ROI) within the breast. The contrast agents are taken up in the blood vessels surrounding a cancerous lesion in the ROI, thereby providing a contrasting image for a period of time with respect to the surrounding tissue, enhancing the ability to locate the lesion.

The use of a contrast agent can be coupled with images of the ROI taken using dual-energy imaging processes and technology. In dual-energy imaging, low-energy (LE) and high-energy (HE) images are taken of the ROI. In particular, CESM (2D) and CE-DBT (3D) imaging modalities are performed with dual-energy technology. For each view (single view in CESM, multiple views for CE-DBT), a pair of images is acquired: 1 low-energy (LE) image, and 1 high-energy (HE) image. In CE-DBT, one can acquire non-paired HE and LE images for each view and still be able to reconstruct HE volume, LE volume and recombined CE volumes for the ROI. For example, HE and LE view can be interleaved during the tomo scan (alternatively HE, LE, HE, LE, HE, LE, etc. . . . ) with a switch from HE to LE then to HE again etc., for each angulated position of the X-ray tube. This is particularly interesting when the tomo scan is performed with a continuous sweep of the X-ray tube, as opposed to the step & shoot approach where images are acquired when the X-ray tube is immobile, enabling the acquisition of HE/LE pairs of images for each specific angle that is considered. The LE and HE images are usually obtained at mean energies above and below the K-edge of the contrast agent. At X-ray energies just above the k-edge of the contrast agent, the absorption of X-rays is increased resulting in an increase of contrast from the iodine contrast agent in the HE image.

In dual-energy 3D or stereotactic procedures, LE and HE image acquisitions are performed, with at least two different positions of the X-ray source with respect to the detector. The images are then recombined to display material-specific information with regard to the internal structure of the tissue being imaged. In the case of 3D CESM, for example, after the injection of contrast medium, dual-energy images are acquired at 2 or more positions of the tube with respect to the detector. For each of these tube angulations, the low and high-energy images are recombined to produce an image of the contrast medium surface concentration at each pixel. The LE and HE images are then recombined to provide an iodine-equivalent or dual-energy (DE) image(s) (for a single view in CESM, and for multiple views for CE-DBT), which in CE-DBT, are used to reconstruct a 3D volume. This description corresponds to the step & shoot mode of acquisition in CE-DBT. Image recombination can be performed based on simulations of the X-ray image chain, which in one suitable exemplary manner is described in United States Patent Application Publication No. 2008/0167552, which is expressly incorporated by reference herein in its entirety, via calibrations on a reference phantom, or any other suitable 3D-reconstruction process, as is known. Additionally, in the continuous mode of acquisition where the X-ray tube moves continuously with interleaved HE and LE images being taken, the LE images are used to reconstruct a LE 3D volume, and the HE images are used to reconstruct a HE 3D volume, with both volumes being recombined in a suitable manner to provide an iodine 3D volume. One can as well implement an algorithm that combines 3D-reconstruction and HE/LE recombination in a single step.

While this process is utilized in both diagnostic and interventional procedures, in one example, a typical contrast-enhanced (CE) dual-energy (DE) stereotactic/3D breast tissue biopsy procedure has one or several of the following steps:

1) Positioning of the patient on the mammography system and breast compression along with injection of contrast agent either prior to or after positioning
2) Acquisition of one or several 0° scout images to check that the lesion is correctly placed in the imaging area to be accessed by the biopsy or treatment mechanism
3) Acquisition at tube angulation A
4) Acquisition at tube angulation B, with B≠A
5) Localization of the lesion on the images acquired at angulation A and B and computation of the (x,y,z) coordinates of the lesion
6) Injection of anesthetics and preparation of the biopsy device
7) Acquisition at tube angulations A and B to check that lesion has not moved (optional)
8) Skin incision and insertion of the biopsy needle
9) Acquisition at tube angulations A and B to check that the needle is correctly positioned (optional)
10) Firing of the biopsy device to take tissue samples
11) Acquisition (at angulation A or B or at 0°) to check correct sampling of tissue (optional)
12) Insertion of biopsy clip (optional)
13) Acquisition to check correct positioning of clip (optional)

In the above method, the steps correspond to a stereo procedure. However, the biopsy can also be performed with the reconstructed 3D volume. Then, in that situation, at least one of the following modified steps of the prior method is employed:

2) Acquisition of one or several DBT images to check that the lesion is correctly placed in the imaging area to be accessed by the biopsy or treatment mechanism
3) Acquisitions at a series of n angles $A_1, A_2, \ldots, A_n$
4) Reconstruction of the 3D volume (usually delivering a set of r images parallel to the detector plane)
5) Localization of the lesion on one image from the reconstructed 3D volume where the targeted lesion is the most visible (which gives the z coordinate of the targeted lesion, the z-coordinate being related to the image number (from 1 to r) in the reconstructed series of images) and reading of the (x,y) coordinates of the lesion in the reconstructed image where the targeted lesion is the most visible.

In steps 7) and 9) one can apply the stereo approach as initially described using the paired angles, or modified steps 3) and 4) as described above using the series of n acquisitions. In step 11) one can also use any of the n angles as described in modified step 3) above.

In the implementation or performance of this procedure, when it is desired to guide a biopsy with CESM or CE-DBT images, it is necessary to generate these DE images at each step of the interventional exam (e.g., scout view, stereo pair or DBT sweep to localize the biopsy target, repeat of stereo pair or DBT sweep to control the position of the interventional device such as a needle, etc.). The primary reason for this is that the dual-energy acquisitions enable the clinician to obtain both morphological and material-specific images for each of these steps.

However, acquiring dual-energy images for each step in the procedure presents certain drawbacks regarding the effects of the procedure on the patient. These include the fact that the number of dual energy acquisitions for each step leads to additional X-ray dose to the patient, which is undesirable. Further, the increased number of usages of the X-ray tube to obtain the required dual energy images consequently increases thermal load placed on the X-ray tube. This can translate to aborted exposures during the procedure, resulting in incomplete images and/or procedure, as well as a decreased life of the X-ray tube based on the increased usage.

In addition, the number of DE images required in the procedure extends the time required for the completion of the procedure that can have an overall length of more than 20 minutes, with the breast or other tissue being imaged being maintained under compression for the entire length of the procedure.

Accordingly, it is desirable to develop a procedure and system for performing diagnostic and interventional, e.g. guided biopsy, procedures that addresses the drawbacks of the currently existing procedures and systems.

BRIEF DESCRIPTION OF THE INVENTION

There is a need or desire for a system and method for performing 3D or stereotactic diagnostic and interventional procedures to image tissue of a patient for examination with a reduced X-ray dose to the patient, and consequent extension of the thermal capability of the X-ray tube, along with a reduction in the overall time required for the completion of the procedure. The above-mentioned drawbacks and needs are addressed by the embodiments described herein in the following description.

According to an exemplary aspect of one embodiment of the invention, dual-energy contrast-enhanced stereotactic imaging processes and systems substitute a single energy, i.e., a low-energy (LE) or high-energy (HE) image, at certain steps in the imaging process utilized in examination and biopsy procedures. The single energy image is combined with opposite energy (LE or HE) image obtained from one or more separate dual-energy imaging steps performed earlier in the localization steps of the method in order to generate material-specific images in a contrast-enhanced dual-energy stereotactic procedure, such as CESM or CE-DBT. In doing so, the system can utilize only single-energy images in the procedure performed by the system once a first set of dual-energy images has been acquired to conduct and/or guide the interventional steps of the method. As a result, the number of images required is reduced, along with the time required for the completion of the procedure, while increasing the operational life of the X-ray tube of the system. This is accomplished by decreasing the number of images per procedure taken by the system, which consequently involves less heating of the X-ray tube and voltage generator, meaning less cooling between image acquisitions is required, further speeding up the procedure.

In particular, in an exemplary embodiment of the invention, to initially determine the location of a region of interest or lesion in tissue to be examined, paired HE/LE (dual energy) images are acquired by the system at a scout view and at a pair of different angles (stereo images). These dual-energy stereo images can be recombined into a contrast-enhanced image and, with the known geometry of the acquisition system, used to localize the projection of the biopsy target on each stereo image of the image pair, and to calculate the 3D coordinates of the target that are used to guide the biopsy process. During the biopsy portion of the method, single energy images can be taken by the system and combined with the opposite energy image obtained from the dual-energy images to provide the contrast-enhanced images for the further guidance/direction for the biopsy procedure.

According to another exemplary aspect of the invention, a method for generating a contrast-enhanced image of tissue for examination includes the steps of acquiring a first image or a first set of images of the tissue and a contrast agent present in the tissue, wherein the first image or the first set of images is or includes at least one single energy image that is either a low energy image or a high energy image, acquiring a number of second images or a second set of images of the tissue and the contrast agent, wherein the number of second images or the second set of images are each a single energy image or include at least one single energy image with an energy level opposite that of the at least one single energy image associated with the first image or the first set of images, and combining the at least one single energy image associated with the first image or the first set of images with the at least one single energy image associated with the number of second images or the second set of images to produce at least one contrast-enhanced image. In at least one embodiment, the method further includes injecting a contrast agent into the tissue.

According to still another exemplary aspect of the invention, a method of performing a contrast-enhanced guided biopsy on tissue includes the steps of acquiring a number of first images of the tissue and the contrast agent at different angles relative to the tissue, wherein the number of first images include one or more single energy images that can be recombined to provide material-specific images, computing coordinates of a region of interest in the tissue, insertion of a biopsy needle into the tissue near the region of interest, acquiring a number of second images at angles corresponding to the angles for the number of first images, wherein the second images are each a single energy image with an energy level opposite that for a subset of images part of the first images, combining at least one of the number of first images and at least one second image to produce the contrast-enhanced image to check that the biopsy needle is correctly positioned within the tissue at the region of interest and firing the biopsy needle to obtain a tissue sample. In at least one embodiment, the method further includes injecting a contrast agent into the tissue.

According to a further exemplary aspect of the invention, an imaging system for acquiring contrast-enhanced images of a tissue injected with a contrast agent includes an energy source in communication with a detector operable to generate a plurality of radiological images of the tissue injected with the contrast agent, a display and a computer connected in communication to display and to receive the acquired plurality of images from the detector, the computer including a memory in communication with a processor, the memory including a plurality of programmable instructions for execution by the processor, the plurality of programmable instructions including acquiring a number of first images of the contrast agent in the tissue, wherein the number of first images are single energy images that are either a low energy image or a high energy image, acquiring a number of second images at angles corresponding to the angles for the number of first images, wherein the second images are each a single energy image with an energy level opposite that for the first images and combining the number of first images with the number of second images to generate a contrast-enhanced output image comprising an illustration of the predicted thickness of the contrast agent for illustration on the display.

According to still a further exemplary aspect of the invention, a method for generating a contrast-enhanced image of tissue for examination includes the steps of acquiring a first set of images of the tissue and a contrast agent present in the tissue, wherein the first set of images includes at least one single energy image that is either a low energy image or a high energy image, acquiring a second set of images of the tissue and the contrast agent, wherein the second set of images includes at least one single energy image with an energy level opposite that for the first image and combining at least one single energy image from the first set of images with at least one single energy image of the second set of images to produce the contrast-enhanced image.

According to still another exemplary aspect of the invention, a method of performing a contrast-enhanced, guided biopsy on tissue including a contrast agent therein includes the steps of acquiring a number of first images of the tissue and the contrast agent at different angles relative to the tissue, wherein the number of first images include at least one of a low energy first image or a high energy first image, computing coordinates of a region of interest in the tissue using the number of first images, acquiring a number of second images of the tissue and the contrast agent at angles corresponding to the angles for the number of first images, wherein the second images include at least one of a low energy second image or a high energy second image and combining at least one of the number of first images and at least one of the number of second images to produce a contrast-enhanced, material specific image to guide a biopsy mechanism with respect to the region of interest.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings

DETAILED DESCRIPTION OF THE DRAWINGS

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
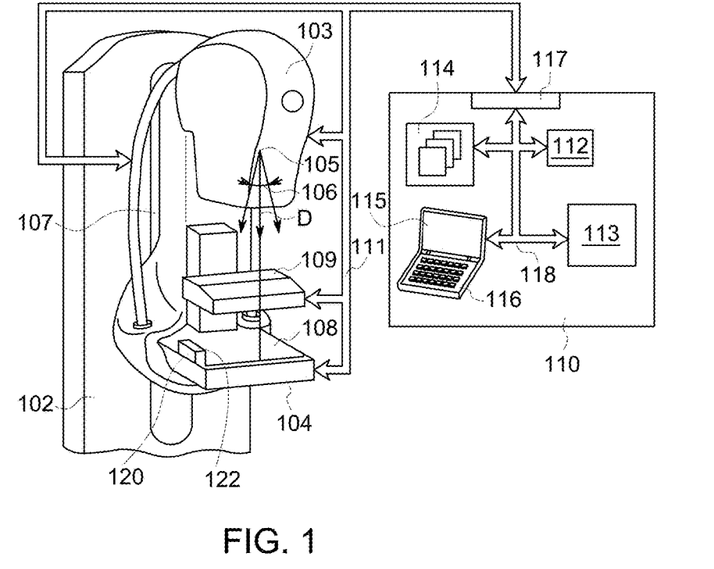
FIG. 1 is a schematic representation of an X-ray device and imaging system according to one exemplary embodiment of the present invention.

FIG. 1 illustrates an X-ray device, especially a mammography machine, according to one exemplary embodiment of the invention. This X-ray device 101, which can be a Senographe Essential® device equipped with the SenoBright® CESM upgrade manufactured by GE Healthcare, or devices similar to those disclosed in U.S. Pat. Nos. 6,714,621; 6,848,826 and 7,693,254, each of which is expressly incorporated herein by reference in its entirety, is capable of emitting X-rays in order to perform dual-energy CESM or CE-DBT diagnostic and/or interventional stereotactic procedures. The device 101 has a vertical column 102. On this vertical column, there is a hinged arm 107 bearing an X-ray-emitting tube 103 and a detector 104 capable of detecting the X-rays emitted by the tube 103. This arm 107 may be oriented vertically, horizontally or obliquely. The tube 103 is provided with a focus 105 which is the X-ray emitting focus. This focus 105 emits an X-ray beam 106 along the direction of emission D.

The arm 107 is hinged on the vertical column 102 in such a way that it enables the tube 103 to be shifted along a path in the shape of an arc of a circle while leaving the detector 104 immobile. However, tomosynthesis and stereo exams can also be implemented with a detector 104 that moves. In these exams, the breast is compressed on a breast support or tray 108 that is stationary, decoupled from the detector 104 and positioned between the X-ray tube 103 and the detector 104.

In a preferred example, the detector 104 is an electronic detector. The detector 104 is hooked to the arm 107 opposite the tube 103 and perpendicular to the direction of emission D so as to receive on its X-ray sensitive area the X-ray beam 106.

The arm 107 is provided with a breast-holder tray 108 on which a patient lays her breast. However, the system and method of the invention is also capable of being utilized to provide contrast-enhanced images of other types of tissue as well. This breast-holder tray 108 is placed on top of the detector 104. The detector 104 is placed beneath the breast-holder tray 108. The detector 104 detects the X-rays that have crossed the patient's breast and the breast-holder tray 108.

Furthermore, for reasons related both to the immobilizing of the breast and to image quality or to limit the intensity of X-rays delivered to the patient's breast, it is necessary to compress the patient's breast during the radiography. Various compression forces may be applied. These forces are applied through a compression paddle 109 which compresses the breast on the breast-holder tray 108 depending on the type of examination to be made. To this end, the arm 107 is capable of being made to compress the breast with the paddle 109 either manually or with a motor-driven means. The paddle 109 is made out of an X-ray transparent material, for example plastic of few millimeters in thickness. The arm 107 therefore bears the following vertically: starting from the top, the X-ray tube 103, the compression paddle 109, the breast-holder tray 108 and the detector 104.

While the paddle 109, the patient's breast, the tray 108 and the detector 104 are fixed, the X-ray tube 103 may take up various positions in space relative to this assembly, such as when the patient is to be examined in a prone or horizontal position. In addition, the device 101 may include or be used with a guiding mechanism 120 positioned adjacent to the tray 108 enabling the accurate positioning of a biopsy or treatment device which may include a biopsy needle 122 for performing a biopsy or a treatment on the part of the body engaged with the device 101. The mechanism 120 can additionally be separate from the device 101, so long as the mechanism 120 can be positioned close enough to the device 101 to enable the mechanism 120 to interact with the patient being examine by the device 101.

In one variant, the detector 104 may be mobile and may take up various positions around the breast at the same time as the X-ray tube 103. In this case, the detector 104 is no longer fixedly joined to the breast-holder tray 108. The detector 104 may be flat or curved. It may be shifted rotationally and/or in translation. In addition, the device 101 may include or be used with a guiding mechanism 120 positioned adjacent to the tray 108 enabling the accurate positioning of a biopsy or treatment device which may include a biopsy needle 122 for performing a biopsy or a treatment on the part of the body engaged with the device 101.

In order to be able to study each part of the patient's breast, the beam 106 may be oriented in a multitude of directions about said breast. After having received a beam 106 which cross a part of the patient's body, the detector 104 emit electrical signals corresponding to the intensity of the X-rays received. These electrical signals may then be transmitted to a control logic unit 110 by means of an external bus 111. These electrical signals enable this control logic unit 110 to produce a projection image corresponding to the part of the body analyzed, as well as a 3D image of the part of the body analyzed in any manners previously described. These images can then be displayed by means of a screen of this control logic unit 110 or printed.

The control logic unit 110 is often made in integrated-circuit form. In one example, the control logic unit 110 comprises a microprocessor 112, a program memory 113, a data memory 114, a display screen 115 provided with a keyboard 116 and an output/input interface 117. The microprocessor 112, the program memory 113, the data memory 114, the display screen 115 provided with a keyboard 116 and the input/output interface 117 are interconnected by an internal bus 118.

In operation, the device 101 is utilized in one or several of the following steps to perform a stereotactic/3D imaging procedure or method:

1. Positioning of the patient on the device 101 and breast compression between paddle 109 and tray 108/detector 104 along with injection of contrast agent either prior to or after positioning
2. Acquisition of one or several 0° scout images to check that the lesion is correctly placed in the imaging area over detector 104 to be accessed by the biopsy or treatment mechanism 120
3. Acquisition of image at tube 103 angulation A
4. Acquisition of image at tube 103 angulation B, with B≠A
5. Localization of the lesion on the images acquired at angulation A and B and computation of the (x,y,z) coordinates of the lesion by control logic unit 110
6. Injection of anesthetics and preparation of the biopsy device/mechanism 120
7. Acquisition of image at tube angulations A and B to check that lesion has not moved (optional)

8. Skin incision and insertion of the biopsy needle 122
9. Acquisition of image at tube 103 angulations A and B to check that the needle 122 is correctly positioned (optional)
10. Firing of the biopsy device 120 to take tissue samples
11. Acquisition of image at tube 103 angulation A or B or at 0° to check correct sampling of tissue (optional)
12. Insertion of biopsy clip (not shown) (optional)
13. Acquisition of image at tube 103 angulation A or B or at 0° to check correct positioning of clip (optional)

In the above method, the steps correspond to a stereo procedure. However, the biopsy can also be performed with the reconstructed 3D volume. Then, in that situation, at least one of the following modified steps of the prior method is employed:
  2) Acquisition of one or several DBT images to check that the lesion is correctly placed in the imaging area to be accessed by the biopsy or treatment mechanism
  3) Acquisitions at a series of n angles $A_1, A_2, \ldots, A_n$
  4) Reconstruction of the 3D volume (usually delivering a set of r images parallel to the detector plane)
  5) Localization of the lesion on one image from the reconstructed 3D volume where the targeted lesion is the most visible (which gives the z coordinate of the targeted lesion, the z-coordinate being related to the image number (from 1 to r) in the reconstructed series of images) and reading of the (x,y) coordinates of the lesion in the reconstructed image where the targeted lesion is the most visible.

In steps 7) and 9) one can apply the stereo approach as initially described using the paired angles, or modified steps 3) and 4) as described above using the series of n acquisitions. In step 11) one can also use any of the n angles as described in modified step 3) above.

In an exemplary embodiment of the invention, the image acquisition performed in steps 2, 3 and 4 is performed using the device 101 to obtain a conventional contrast-enhanced dual-energy image acquisition. As such, the device 101 is operated to obtain a LE image and an HE images at the 0° position for the tube 103, and at the angular positions identified as A and B in steps 3 and 4. These LE and HE images are subsequently stored in memory 114 after acquisition. For the remainder of the procedure, and in particular with regard to each of steps 7, 9, 11 and 13, when performed, the images in each of one or more of these steps are acquired using a single-energy acquisition process, which can be either a LE process or a HE process. To generate the material-specific images for steps 7, 9, 11 and 13, the single-energy LE or HE images obtained in these steps are combined with the opposite energy level (LE or HE) images obtained from one or more of steps 2, 3 and 4.

In one exemplary embodiment of the invention, if HE images are acquired at one or more of steps 7, 9, 11 and 13, then these HE images are combined with the LE images acquired at one or more of steps 2, 3 and 4 to generate material-specific images for each step in a suitable manner, such as that described in US Patent Application Publication No. 2008/0167552, expressly incorporated by reference herein in its entirety, or via calibrations on a reference phantom, or other suitable image combination method.

In another exemplary implementation of the invention, because patient, i.e., breast or tissue, motion may occur between the dual-energy acquisitions in steps 2, 3 and 4 and the single energy acquisitions in one or more of steps 7, 9, 11 and 13, image registration can be performed between the single-energy image from each of step 7, 9, 11 and/or 13 and the opposite energy image obtained from steps 2, 3 and 4, before the combination of these images into a material-specific image. One example of image registration of this type is a local rigid registration scheme, as described in Jeunehomme, F. "MAMMOGRAPHIE NUMERIQUE AVEC INJECTION DE PRODUIT DE CONTRASTE". PhD dissertation, Université Parix XI Orsay, no 7860, April 2005, expressly incorporated by reference herein in its entirety.

Figure 2:
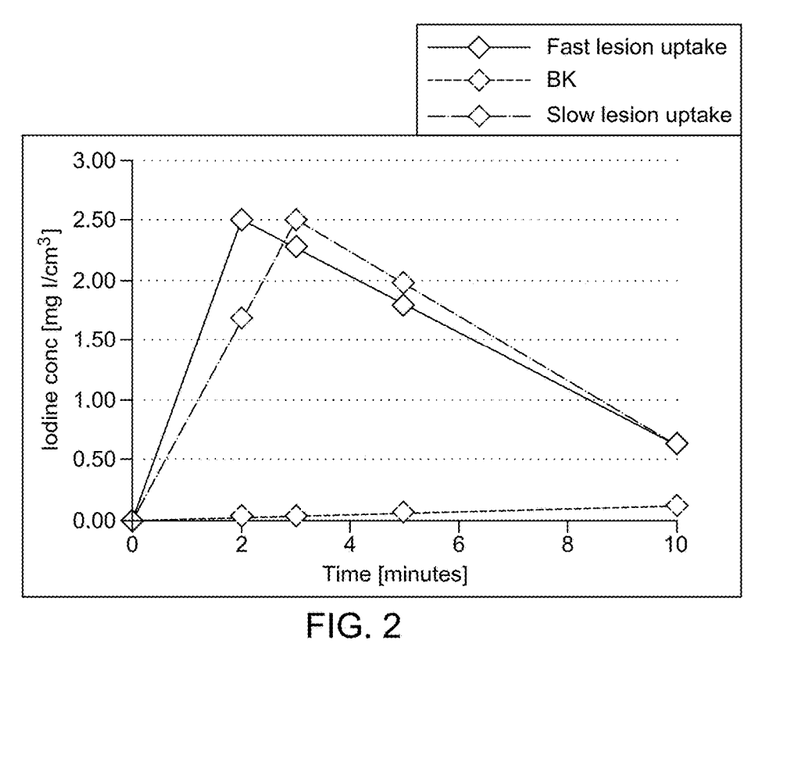
FIG. 2 is a graphic representation of a representative iodine contrast agent volumetric uptake curves according to an exemplary embodiment of the invention.
Figure 3:
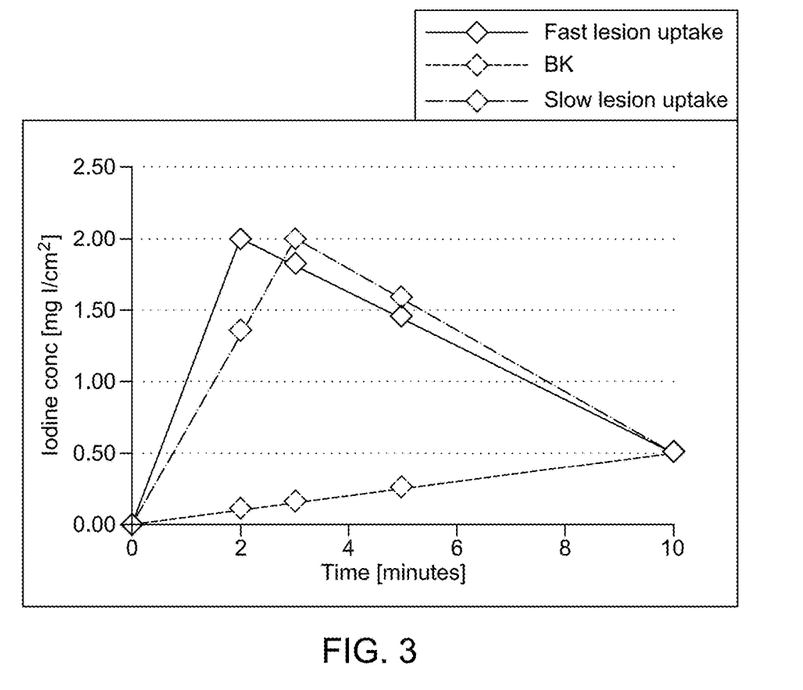
FIG. 3 is a graphic representation of a representative iodine contrast agent area uptake curves according to an exemplary embodiment of the invention.

Referring now to FIGS. 2 and 3, in evaluating the ability of the system/device 101 and method of the invention to provide images comparable to those obtained as a result of a conventional contrast-enhanced, dual-energy stereotactic procedure, the speed of uptake of the contrast agent utilized is illustrated. In the exemplary embodiment, with iodine as the selected contrast agent, the peak volumetric and area concentrations are shown for early and late uptake of the contrast agent into the lesion to be imaged. In each illustrated case, the window for the peak uptake of the contrast agent occurs between approximately two (2) minutes and three (3) minutes from initial injection of the contrast agent into the tissue. Also, as illustrated in FIGS. 2 and 3, the concentration increases quickly to the peak values for early and late uptake, and then experiences a significant concentration reduction or washout from the peak values at 2-3 minutes to near background tissue concentrations at ten (10) minutes from injection.

Figure 4:
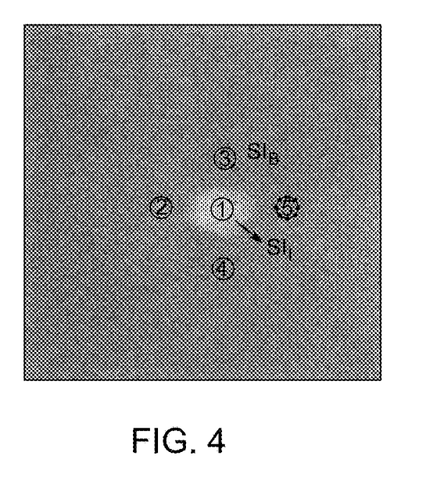
FIG. 4 is graphic representation of an exemplary method to perform signal difference-to-noise ratio (SDNR) calculation on material-specific images according to an exemplary embodiment of the invention.
Figure 5A:
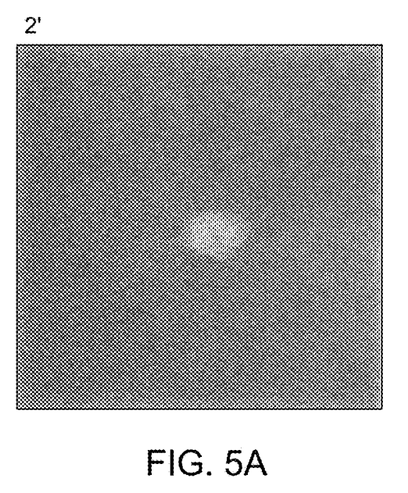
FIGS. 5A-5D are simulated uptake images of a lesion, assuming an early peak contrast uptake of the lesion, taken at 2, 3, 5 and 10 minutes after administration of a contrast agent using a conventional paired, dual-energy system and method.
Figure 5B:
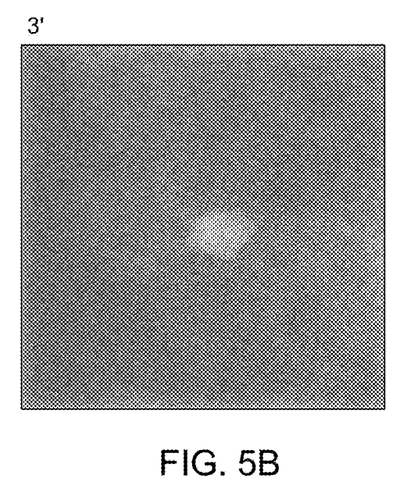
Figure 5C:
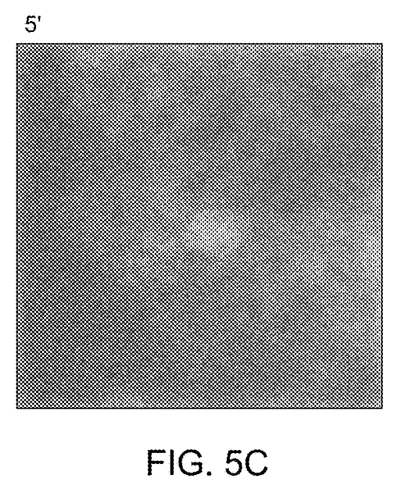
Figure 5D:
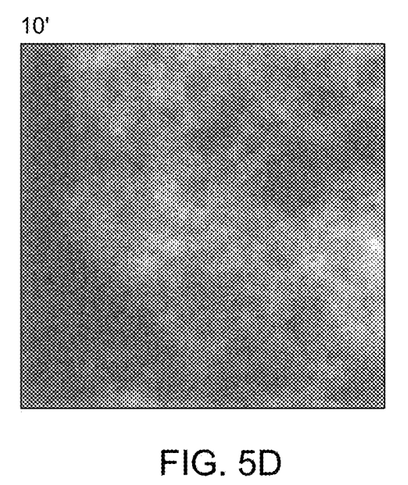
Figure 6A:
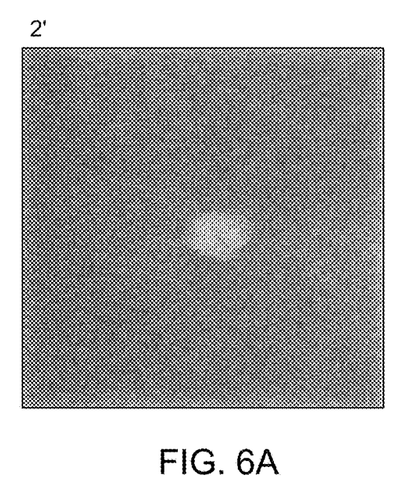
FIG. 6A is a simulated uptake image of a lesion, assuming an early peak contrast uptake of the lesion, obtained from the recombination of LE and HE images acquired at 2 minutes after injection of a contrast agent.
Figure 6B:
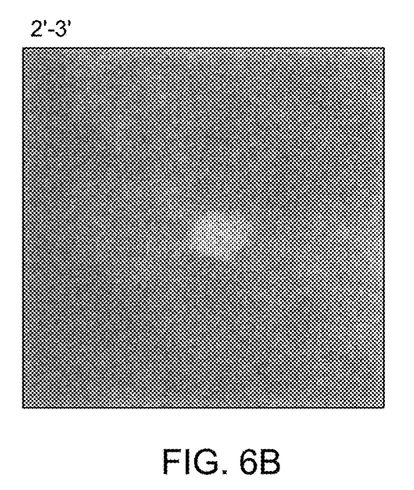
FIGS. 6B-6D are respectively simulated uptake images of the same lesion obtained from the combination of HE images acquired respectively at 3, 5 and 10 minutes after administration of a contrast agent with the LE image acquired at 2 minutes according to an exemplary embodiment of the invention.
Figure 6C:
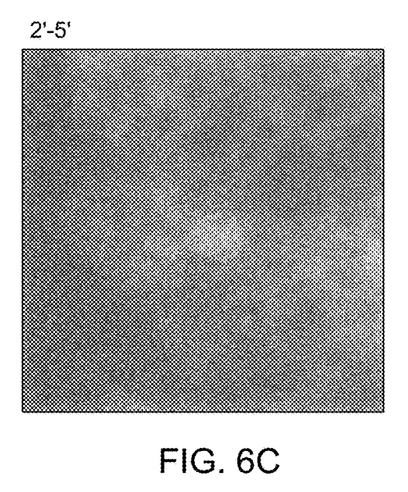
Figure 6D:
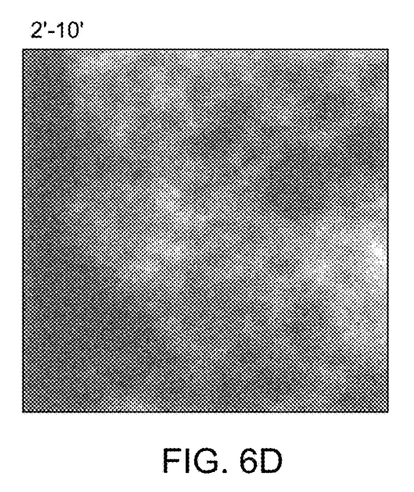
Figure 7A:
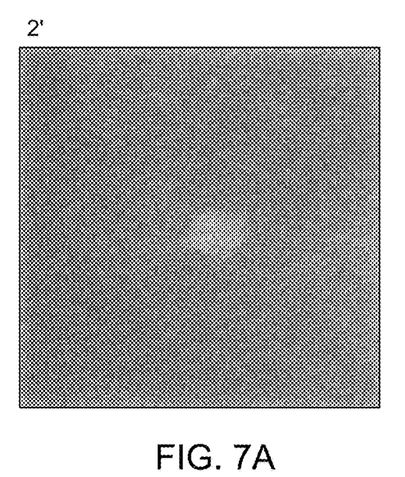
FIGS. 7A-7D are simulated uptake images of a lesion, assuming a late peak contrast uptake of the lesion, taken at 2, 3, 5 and 10 minutes after administration of a contrast agent using a conventional paired, dual energy system and method.
Figure 7B:
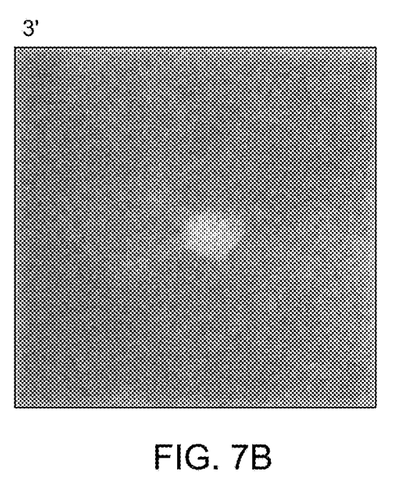
Figure 7C:
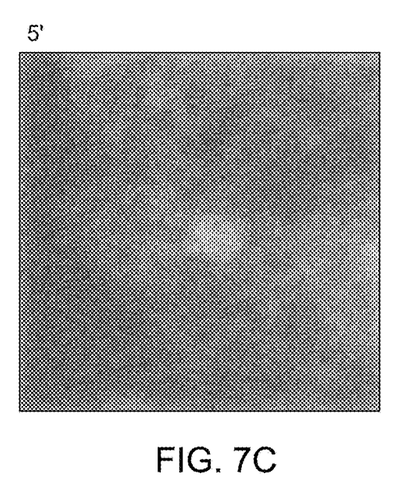
Figure 7D:
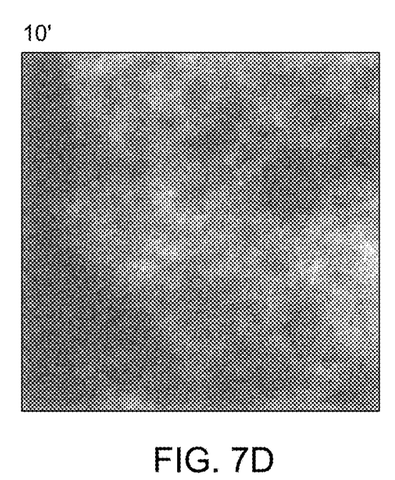
Figure 8A:
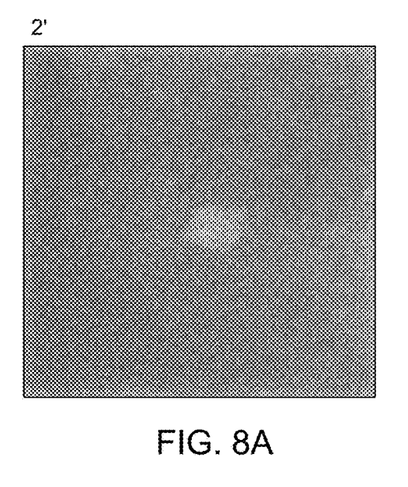
FIG. 8A is a simulated uptake image of a lesion, assuming a late peak contrast uptake of the lesion, obtained from the recombination of LE and HE images acquired at 2 minutes after injection of a contrast agent.
Figure 8B:
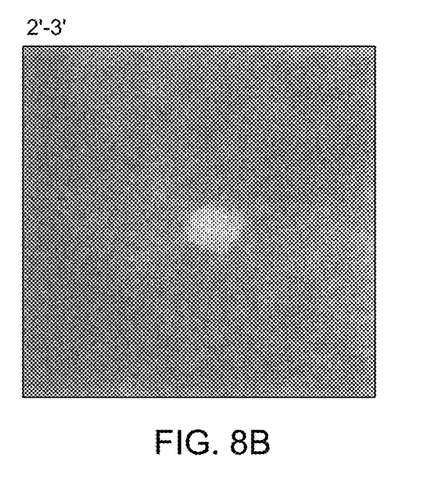
FIGS. 8B-8D are respectively simulated uptake images of the same lesion obtained from the combination of HE images acquired respectively at 3, 5 and 10 minutes after administration of a contrast agent with the LE image acquired at 2 minutes according to an exemplary embodiment of the invention.
Figure 8C:
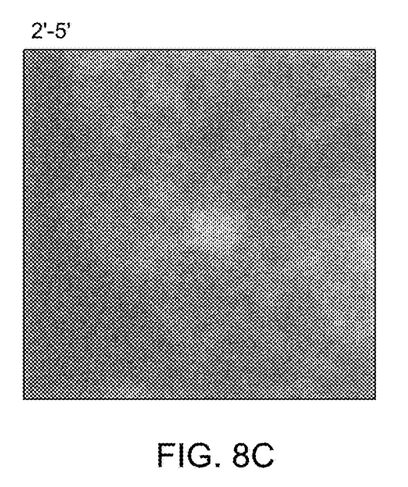
Figure 8D:
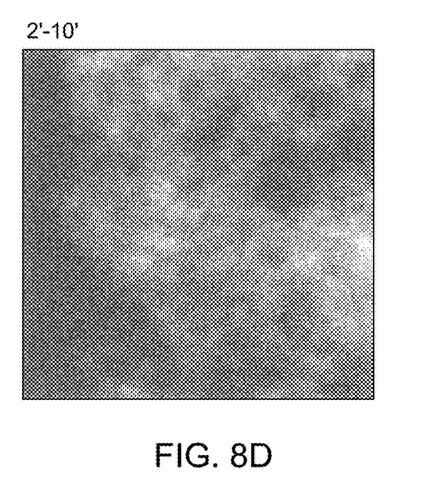

As a result, to compare the ability of the system/device 101 and method of the invention with conventional contrast-enhanced, dual-energy stereotactic methods, i.e., CESM, images of stereotactic procedures using conventional CESM and the system and method of the invention have been evaluated using simulated images of a breast with a lesion containing iodine as the contrast enhancing agent at different angulations. In performing the comparison, as shown in FIG. 4, measurements of the signal difference-to-noise ratio (SDNR) using the simulated acquired images of the breast were determined for each acquisition process by calculating signal intensities for the iodine (Sit) within the lesion or ROI, and for the background tissue (SI) at positions 1-5. These signal intensity values in the background tissue were utilized to determine a standard deviation for the iodine signal intensity in the background tissue, which was used in the following equation to derive the SDNR for each image:

$$SDNR = \frac{(SI_I - SI_B)}{\sigma_I}$$

For the conventional images and SDNR analysis, the images were LE and HE images taken of the breast at 2', 3', 5' and 10' from start of injection of the iodine contrast agent used in a conventional dual-energy CESM process. The material-specific images resulting of the combination of the paired LE and HE images assuming an early uptake of the iodine contrast agent are illustrated in FIGS. 5A-5D, and the material-specific images resulting of the combination of the paired LE and HE images assuming a late uptake of the iodine contrast agent are illustrated in FIGS. 7A-7D.

To illustrate one possible implementation of the process of the invention to obtain material-specific images resulting of the combination of LE and HE images of the breast, for both an early uptake as shown in FIGS. 6A-6D and a late uptake as shown in FIGS. 8A-8D, the image taken at 2' is a dual-energy image having LE and HE component images, while the images at 3', 5; and 10' are HE images. These HE images at 3', 5' and 10' were subsequently combined with the LE image taken at 2' using the image recombination scheme as described in United States Patent Application No. 2008/0167552, previously incorporated by reference herein. As shown by the images in FIGS. 6A-6D and 8A-8D, the images show a good texture cancellation and visibility of iodine. Alternatively, another possible implementation of the system and method of the invention can be to combine the HE image taken at 2' with LE images taken at 3', 5' and 10'.

Figure 9:
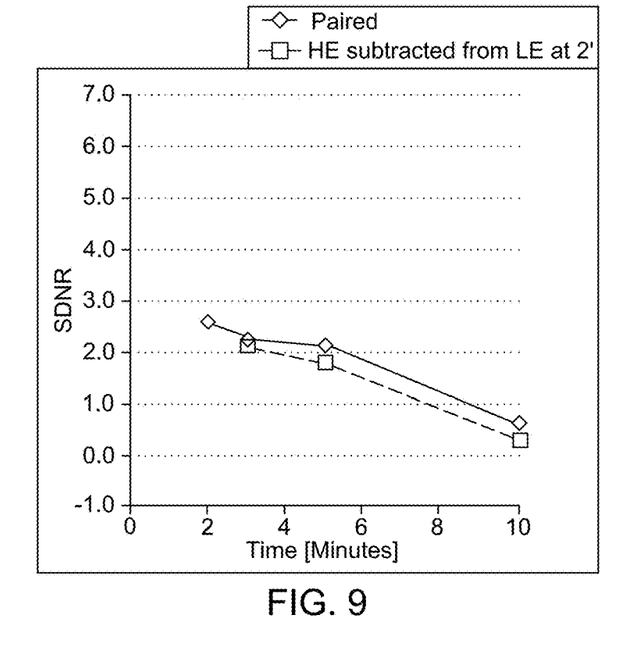
FIG. 9 is a graphic representation of comparative SDNR curves, assuming an early peak contrast uptake of the lesion, computed, as described in FIG. 4, on recombined images resulting on one hand from the combination of LE and HE paired images acquired at 2, 3, 5 and 10 minutes after administration of a contrast agent, and on the other hand from the combination of HE images acquired respectively at 3, 5 and 10 minutes after administration of a contrast agent with the LE image acquired at 2 minutes according to an exemplary embodiment of the invention.
Figure 10:
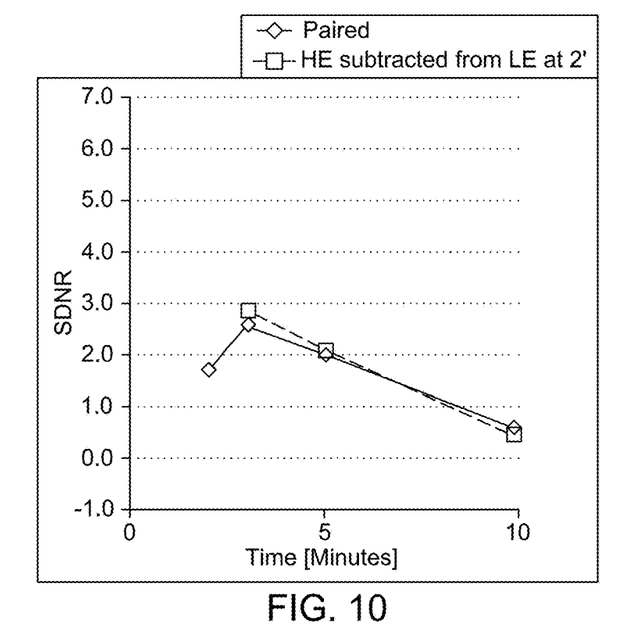
FIG. 10 is a graphic representation of comparative SDNR curves assuming a late peak contrast uptake of the lesion, computed, as described in FIG. 4, on recombined images resulting on one hand from the combination of LE and HE paired images acquired at 2, 3, 5 and 10 minutes after administration of a contrast agent, and on the other hand from the combination of HE images acquired respectively at 3, 5 and 10 minutes after administration of a contrast agent with the LE image acquired at 2 minutes according to an exemplary embodiment of the invention.

Using the SDNR values obtained from the images taken of the breast in the conventional dual-energy CESM procedure and the process of the invention, FIG. 9 illustrates the differences in SDNR values for the procedures assuming an early contrast uptake, while FIG. 10 illustrates the differences assuming a late contrast uptake. FIG. 9 for the values obtained from these simulations shows that in the case of an over-estimation of the iodine concentration in the LE images at one or more of steps 7, 9, 11 and/or 13, the iodine SDNR in the recombined images obtained from the combination of a high-energy image, such as would be obtained in the method of the invention at one or more of steps 7, 9, 11 and/or 13 with a low-energy image obtained at step 3 and/or 4, may be even higher than for paired dual-energy images. FIG. 10 for the values obtained from these simulations shows that in the case of an under-estimation of the iodine concentration in the LE images at one or more of steps 7, 9, 11 and/or 13, the iodine SDNR in the recombined images obtained from the combination of a high-energy image, such as would be obtained in the method of the invention at one or more of steps 7, 9, 11 and/or 13 with a low-energy image obtained at step 3 and/or 4, may be lower than for paired dual-energy images, but still high enough to the visualization of the contrast uptakes.

In alternative exemplary embodiments, the system and method of the invention for imaging during a biopsy procedure enables the localization of the 3D coordinates of a biopsy target in a lesion visible through its contrast uptake in multiple energy contrast-enhanced x-ray imaging, and the ability to generate material-specific images allowing to control the position of tools such as needles relative to the contrast uptake in the lesion.

In a stereo approach in one exemplary embodiment, at least two (2) images (LE or HE) are acquired at two (2) different angles to form a set of first images. This set of first images is utilized in a stereo computation of the 3D coordinates of the lesion or target. Subsequently, at least two (2) additional images are acquired at two (2) different angles, which are the same as for the set of first images, in order to form a set of second images. This set of second images is taken at an energy level opposite at least one of the set of first images, and then combined with that first image to provide a display of a material-specific image to provide guidance and control the position of the treatment or biopsy tool(s) in the tissue being imaged, such as the breast.

With regard to the stereo approach, in exemplary embodiments of the invention, the general steps of the method can be as follows:

Acquisition of LE1/HE1 images for each projection of the breast within the set of first images+acquisition of LEi/HEi images for each projection of the breast within the set of second images (i being a given time point amongst T time points different from 1)+LEk/HEk recombination leading to a material-specific image (with k=1 or i).

Acquisition of LE1/HE1 images for each projection of the breast within the set of first images+acquisition of HEi (or alternatively LEi) images for each projection of the breast within the set of second images+LE1/HE1 recombination leading to a material-specific image for each projection of the breast within the set of first images and LE1/HEi (or alternatively LEi/HE1) recombination leading to a material-specific image for each projection of the breast within the set of second images.

Acquisition of LE1 (or alternatively HE1) images for each projection of the breast within the set of first images+acquisition of HEi (or alternatively LEi) images for each projection of the breast within the set of second images+LE1/HEi (or alternatively LEi/HE1) recombination leading to a material-specific image for each projection of the breast within the set of second images.

In a digital breast tomosynthesis approach, in an exemplary embodiment of the invention, a set of N images acquired at N different angles forms the set of first images, which are utilized in 3D-tomographic reconstruction leading to a set of R reconstructed images of the breast volume. With the reconstructed images, a computation of the z-coordinate of the target or lesion in the breast is performed by selecting of one out of the R reconstructed images where the lesion is best depicted and computing the x- and y-coordinates of the target by selecting one target point in the selected reconstructed image. To guide and control a biopsy tool into contact with the lesion, subsequently a set of N images acquired at N different angles, which can be the same or different than those for the set of first images, is acquired to form the set of second images. The set of second images are used in conjunction with the set of first images in 3D-tomographic reconstruction leading to a set of R reconstructed images of the breast volume that can be displayed to guide and control the position of tools in the breast during the examination or biopsy procedure.

With regard to the digital breast tomosynthesis (DBT) approach, in exemplary embodiments of the invention, the general steps of the method can be as follows:

Acquisition of paired LE/HE images for each projection of the breast+LE/HE recombination leading to a material-specific image for each projection of the breast.

Acquisition of LE1/HE1 images for each projection of the breast within the set of first images+acquisition of HEi (or alternatively LEi) images for each projection of the breast within the set of second images+LE1/HE1 recombination leading to a material-specific image for each projection of the breast within the set of first images and LE1/HEi (or alternatively LEi/HE1) recombination leading to a material-specific image for each projection of the breast within the set of second images.

Acquisition of LE1 (or alternatively HE1) images for each projection of the breast within the set of first images+acquisition of HEi (or alternatively LEi) images for each projection of the breast within the set of second images+LE1/HEi (or alternatively LEi/HE1) recombination leading to a material-specific image for each projection of the breast within the set of second images.

In additional exemplary embodiments of the invention, the acquisition steps for the first images and second images can be a mix of stereo acquisition steps and DBT acquisition steps and image reconstruction within the same procedure. Also, images taken using more than two (2) energy levels can also be utilized, e.g., images taken at three (3) energies for a triple-energy contrast enhanced x-ray imaging process.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for generating at least one contrast enhanced image of tissue comprising a contrast agent, the method comprising:
    acquiring a first set of images of the tissue at one or more angles relative to the tissue, wherein the first set of images comprises at least one low energy single energy image taken at a first angle and at least one high energy single energy image taken at a second angle, and wherein the first angle is different than the second angle;
    combining the at least one low energy single energy image and the at least one high energy single energy image to obtain at least one recombined image;
    determining coordinates of a region of interest in the tissue from the at least one recombined image;
    acquiring a second set of images of the tissue, wherein the second set of images comprises at least one of a high energy single energy image and a low energy single energy image; and
    producing a plurality of contrast-enhanced images by at least one of (i) combining each high energy single energy image from the second set of images with the at least one low energy single energy image from the first set of images, and (ii) combining each low energy single energy image from the second set of images with the at least one high energy single energy image from the first set of images.

2. A method for generating at least one contrast enhanced image of tissue comprising a contrast agent, the method comprising:
    acquiring a first set of images of the tissue at one or more angles relative to the tissue, wherein the first set of images comprises at least one low energy single energy image taken at a first angle and at least one high energy single energy image taken at a second angle;
    combining the at least one low energy single energy image and the at least one high energy single energy image to obtain at least one recombined image;
    determining coordinates of a region of interest in the tissue from the at least one recombined image;
    acquiring a second set of images of the tissue, wherein the second set of images comprises at least one single energy image; and
    producing at least one contrast-enhanced image by at least one of (i) combining the at least one single energy image from the second set of images with the at least one low energy single energy image from the first set of images, if the at least one single energy image from the second set of images is a high energy image, and (ii) combining the at least one single energy image of the second set of images with the at least one high energy single energy image from the first set of images, if the at least one single energy image from the second set of images is a low energy image,
    wherein the first angle is different than the second angle.

3. The method of claim 2, wherein the second set of images are acquired before the first set of images.

4. The method of claim 2, wherein the step of acquiring the second set of images comprises acquiring each of the second set of images at different times from the acquisition of the first set of images.

5. The method of claim 2, wherein the coordinates are two-dimensional coordinates.

6. The method of claim 2, wherein the coordinates are three-dimensional coordinates.

7. The method of claim 2, wherein the step of acquiring the first set of images comprises acquiring the first set of images in a spectral mammography procedure.

8. The method of claim 2, wherein the step of acquiring the first set of images comprises acquiring the first set of images in a digital breast tomosynthesis procedure.

9. The method of claim 2, further comprising
    positioning a biopsy needle to reach the region of interest using at least the determined coordinates; and
    performing a biopsy procedure comprising inserting the biopsy needle into the tissue and extracting a tissue sample from the region of interest.

10. The method of claim 9, wherein the at least one image from the second set of images is acquired during the biopsy procedure.

11. The method of claim 10, wherein the at least one image from the second set of images is used to further guide the biopsy needle.

12. A method for generating at least one contrast enhanced image of a tissue comprising a contrast agent, the method comprising:
    acquiring a first set of images of the tissue at at least two angles relative to the tissue, wherein the first set of images comprises at least one low energy single energy image taken at a first angle and at least one high energy single energy image taken at a second angle, and wherein the first angle is different than the second angle;
    generating, using tomographic reconstruction, at least one low energy image set from the at least one low energy single image;
    generating, using tomographic reconstruction, at least one high energy image set from the at least one high energy single energy image;
    combining the at least one low energy image set with the at least one high energy image set to obtain at least one recombined image set;
    determining coordinates of a region of interest in the tissue from the at least one recombined image set;
    acquiring a second set of images of the tissue, wherein the second set of images comprises at least one single energy image; and
    producing at least one contrast-enhanced image by at least one of (i) combining the at least one single energy image from the second set of images with at least one low energy single energy image from the first set of images, if the at least one single energy image from the second set of images is a high energy image, and (ii) combining the at least one single energy image of the second set of images with at least one high energy single energy image from the first set of images, if the at least one single energy image from the second set of images is a low energy image.

13. An imaging system for acquiring contrast-enhanced images of a tissue comprising a contrast agent, the imaging system comprising:
    an energy source in communication with a detector, the detector operable to generate a plurality of radiological images of the tissue;

a display; and a computer connected in communication with the display and the detector, wherein the computer is configured to:

acquire a first set of images of the tissue comprising at least one low energy single energy image and at least one high energy single energy image, wherein the first set of images comprises at least one low energy single energy image taken at a first angle and at least one high energy single energy image taken at a second angle, and wherein the first angle is different than the second angle;

combine the at least one low energy image with the at least one high energy image to obtain at least one recombined image and determine coordinates of a region of interest in the tissue from the at least one recombined image;

acquire a second set of images of the tissue comprising at least one single energy image; and produce at least one contrast-enhanced image by at least one of (i) combining the at least one single energy image from the second set of images with the at least one low energy single energy image from the first set of images, if the at least one single energy image from the second set of images is a high energy image, and (ii) combining the at least one single energy image of the second set of images with the at least one high energy single energy image from the first set of images, if the at least one single energy image from the second set of images is a low energy image.

14. The imaging system of claim 13, wherein the contrast-enhanced image comprises an illustration of a predicted uptake of the contrast agent.

15. The imaging system of claim 13, wherein the computer is further configured to identify the region of interest from the at least one contrast-enhanced image.

16. The imaging system of claim 13, further comprising a biopsy mechanism comprising a movable needle set configured to extract a tissue sample from the region of interest.

* * * * *

UNITED STATES PATENT AND TRADEMARK OFFICE
CERTIFICATE OF CORRECTION

PATENT NO.        : 10,398,397 B2
APPLICATION NO.   : 14/587522
DATED             : September 3, 2019
INVENTOR(S)       : Serge Louis Wilfrid Muller et al.

Page 1 of 1

It is certified that error appears in the above-identified patent and that said Letters Patent is hereby corrected as shown below:

In the Claims

Claim 12, Column 14, Line 39, after "single" insert -- energy --.

Signed and Sealed this
Twenty-second Day of October, 2019

Andrei Iancu
*Director of the United States Patent and Trademark Office*